United States Patent [19]

Clyde

[11] 4,446,236

[45] May 1, 1984

[54] APPARATUS FOR A PHOTOCHEMICAL REACTION

[76] Inventor: Robert A. Clyde, P.O. box 983, Asheville, N.C. 28802

[21] Appl. No.: 407,299

[22] Filed: Aug. 11, 1982

[51] Int. Cl.³ .................. C12M 1/00; B01D 33/34; C10J 1/18; B01J 16/00

[52] U.S. Cl. .................. 435/287; 435/288; 435/312; 435/313; 435/315; 435/316; 435/813; 435/818; 422/186; 422/186.30; 210/150; 210/96.1; 261/92

[58] Field of Search .............. 435/287, 288, 312, 313, 435/315, 316, 813, 818; 422/186, 186.30, 135, 240, 287, 288; 210/150; 261/92

[56] References Cited

U.S. PATENT DOCUMENTS 3,314,768  4/1967  Ebrey .................. 422/186
3,594,277  7/1971  Mako .................. 435/315
3,733,062  5/1973  Bracich .................. 261/92

Primary Examiner—Robert J. Warden
Assistant Examiner—William J. Herald
Attorney, Agent, or Firm—D. I. Hague

[57] ABSTRACT

A photochemical reactor is divided into a first section suitable for containing a volume of fluid to be reacted and a second section having at least one light transmitting wall. A porous, high area, fiber webbing is mounted within the reactor so that at least a portion of the webbing is immersed in the fluid. The webbing is moved within the reactor so that the webbing is sequentially immersed in the fluid contained in the first reactor section and then moved to the second reactor section whereat the fluid attached to the webbing is exposed to light transmitted through the light transmitting wall.

8 Claims, 3 Drawing Figures

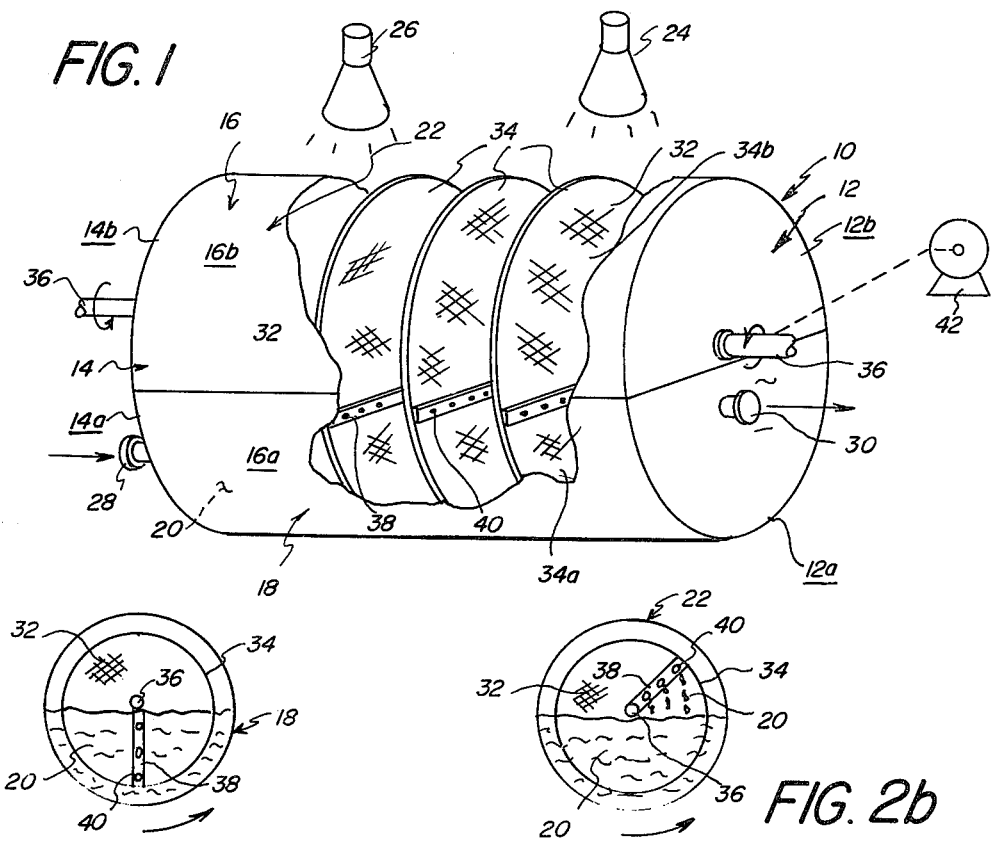
FIG. 1
FIG. 2a
FIG. 2b
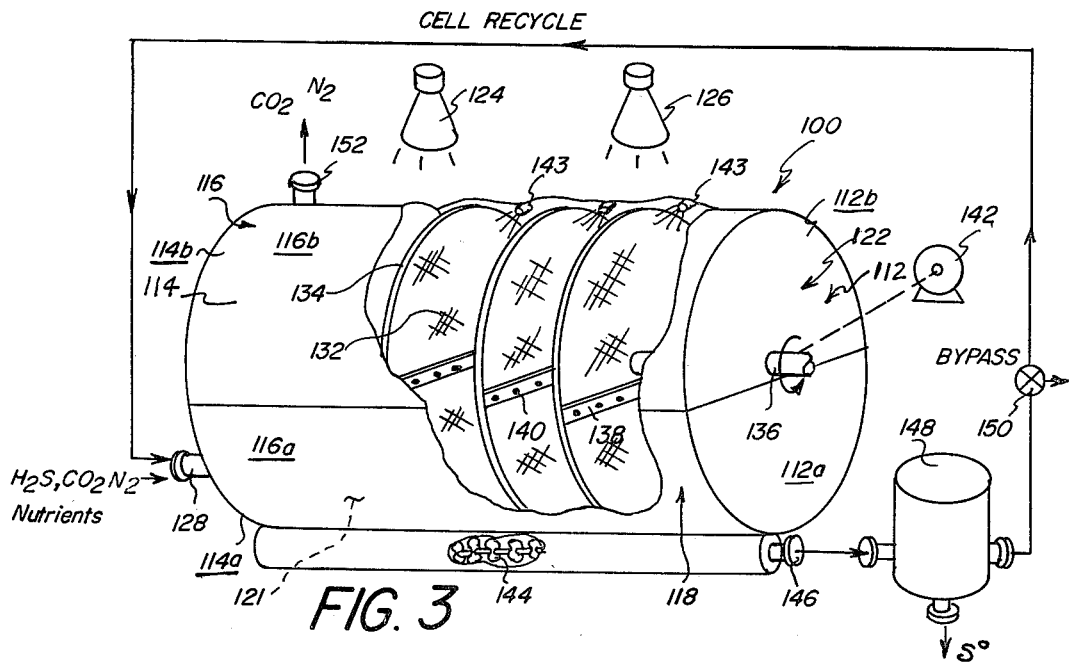
FIG. 3

APPARATUS FOR A PHOTOCHEMICAL REACTION

BACKGROUND OF THE INVENTION

1. Field of the Invention

The present invention is concerned generally with the field of photochemistry. More particularly, the invention relates to apparatus specifically adapted for treating a liquid or gas fluid of photometabolism (photosynthesis or biophotolysis).

2. Description Relative to the Prior Art

The science of photochemistry is based on the interaction of molecules with quanta of light to produce unique chemical and physical changes in matter. The benefits of photochemistry, which include simplicity of control and the absence of undesired side effects, have led to applications for treating toxic wastes. A recent example is a specially designed extraction photolysis process for destroying dioxin described in an article entitled "Destroying Dioxin: A Unique Approach" appearing in the October 1980 publication of Waste Age.

It is also well known that certain microorganisms in the presence of light and appropriate nutrient medium undergo photosynthetic reactions which can be used (1) to remove pollutants, such as hydrogen sulfide ($H_2S$) and carbon dioxide ($CO_2$), from industrial gas streams as described in a paper entitled "Bioprocess For Fossil Fuel Acid-Gas Bioconversion—An Alternative To The Stretford Process" presented at the Gatlinburg Conference on Biotechnology, May 11-14, 1982, and (2) to produce useful chemicals such as molecular hydrogen as described in U.S. Pat. No. 4,010,076, to Weetall.

In order to attain a high yield, it can be readily appreciated that it is desirable to provide the greatest possible exposure area between the light and the molecules of the treated fluid to be photoelectronically excited. In those applications in which photosynthetic microorganisms are used, it is also desirable to provide the greatest possible contact area between the microorganism and the selected components of the treated fluid which are to be converted into selected chemicals. One disadvantage of the photochemical reactor apparatus described in the above noted prior art is that their efficiency is low because much of the light is blocked or absorbed by the fluid volume, which is often colored, and therefore is not available to initiate the desired photochemical reactions.

SUMMARY OF THE INVENTION

The present invention provides a photochemical reactor apparatus with improved light utilization efficiency. The improved light utilization efficiency is achieved in accordance with the teachings of the present invention by dividing the reactor into a first section suitable for containing the volume of fluid to be reacted and a second section having at least one light transmitting wall. A fluid input port and a fluid output port communicate with the first reactor section and the environment external to the reactor. A porous support substrate is mounted within the reactor so that at least a portion of the support substrate is immersed in the fluid contained in the first reactor section. The support substrate which comprises a multiplicity of high area fibers is moved within the reactor so that the substrate is sequentially immersed in the fluid contained in the first reactor section and then moved into the second reactor section whereat the fluid attached to the fibers is exposed to light transmitted through the light transmitting wall. The high area fibers provide an extremely large surface area for exposure of the fluid to the light. Advantageously, in those applications using photosynthetic microorganisms, the high area fibers also provide an extremely large surface area for contact of the microorganism and the treated fluid.

The invention and its features and advantages will become more apparent by referring to the accompanying drawings and to the ensuing description of the preferred embodiments.

BRIEF DESCRIPTION OF THE DRAWINGS

FIG. 1 is a schematic, perspective view of a reactor constructed in accordance with the present invention;

FIGS. 2A and 2B are end views showing the sequence of movement of a fiber support disc; and FIG. 3 is a schematic, perspective view of an alternative embodiment of the reactor.

DETAILED DESCRIPTION OF THE INVENTION

Because photochemical reactors are well known, the present description will be directed in particular to elements forming part of, or cooperating directly with, apparatus in accordance with the present invention. It is to be understood that elements not specifically shown or described may take various forms well known to those having skill in the photochemical reactor art.

Referring now to FIGS. 1 and 2, a photochemical reactor 10 incorporating the features of this invention includes a hollow container having a front wall 12, a rear wall 14 and a cylindrical side wall 16. A first sector 18 of the reactor 10, comprising the lower portions 12a, 14a and 16a, respectively, of the front, rear and side walls is adapted to contain a volume of a selected fluid 20 to be photochemically reacted. A specific example of a selected fluid is a toxic liquid waste comprising a mixture of organic solvent and dioxin.

A second sector 22 of the reactor is comprised of the upper portions 12b, 14b and 16b, respectively, of the front, rear and side walls. As shown in FIG. 1, the upper cylindrical side wall 16b is at least translucent and preferably transparent to the radiation emitted by a pair of light sources 24 and 26 mounted above the upper side wall 16b by means (not shown). It will be understood, however, that the upper front and rear walls 12b and 14b could also be transparent and furthermore that the number and location of the light sources 24 and 26 could be varied as desired.

A fluid input port 28 located in the lower rear wall portion 14a and a fluid output port 30 located in the lower front wall portion 12a communicate with the first reactor sector 18 and the environment external to the reactor.

A plurality of porous support discs 34 are rotatably mounted on a shaft 36 which is journaled in the front and rear walls 12 and 14 of the container so that a lower portion 34a of each disc is immersed in the fluid 20 contained in the reactor sector 18 and an upper portion 34b of each disc extends into the reactor sector 22. A high area fiber webbing 32 is attached to each of the discs 34. The fiber webbing 32 may be made of any suitable high surface area material such as polyester, orlon, fiberglass, organic aramid fibers such as Nomex and Kevlar manufactured by E. I. DuPont Co. or ceramic fibers such as Fiberfax manufactured by Carborundum, Nextel manufactured by 3M, Celiox manufactured by Celanese, Zetex manufactured by Newtex Industries and Refrasil manufactured by Armco. To create an even greater surface area, a high area alumina, such as collodial alumina identified as Baymal and provided by E. I. DuPont, can be applied to the fiber webbing 32. Preferably, the webbing 32 is about one quarter inch or less apart and made of fibers about one eighth inch in diameter or less.

As best shown in FIGS. 2A and 2B, each support disc 34 has at least one hollow tube 38 extending between the centrally located shaft 36 and the outer periphery of the disc 34. The tube 38 is provided with a plurality of holes 40 which function to intake fluid 20 into the tube 38 when the tube is located in the reactor sector 18 and subsequently to distribute such fluid over the webbing 32, in the manner explained in detail hereinbelow, when the tube is located in the reactor sector 22.

In operation of the reactor 10, the lower sector 18 is filled with fluid 20 through the input port 28. The light sources 24 and 26, and a motor 42 which is coupled (by means not shown) to the shaft 36 are then turned on. The light sources 24 and 26 provide radiation of a wavelength which excites selected molecules of the fluid being treated. In the aforementioned extraction photolysis process used to destroy dioxin, ultraviolet light is used to initiate the desired photochemical reaction and accordingly, light sources 24 and 26 provide ultraviolet light. If desired, the ultraviolet light sources 24 and 26 can be cooled with water by means not shown.

As the shaft 36 is rotated by the motor 42, the discs 34 complete a sequence of cylical movements illustrated in FIGS. 2A and 2B. As shown in FIG. 2A, when a disc 34 is rotated to a position so that the hollow tube 38 is immersed in the fluid 20 contained in the reactor sector 18, the tube 38 is filled with fluid via the tube holes 40. As the disc continues its rotation the tube 38 is rotated out of the fluid 20 and into the reactor sector 22. As shown in FIG. 2B gravity then causes the fluid 20 to run down the tube 38 and out the holes 40 where it is evenly distributed in a thin coat over the surface of the fiber webbing 32. Advantageously, the fluid wetted, high area fiber webbing 32 provides a large exposure area for the light sources 24 and 26 which increases the efficiency of the desired photochemical reaction.

An alternative embodiment of an anaerobic reactor 100 adapted to remove hydrogen sulfide (H$_2$S) from industrial gas streams using the photosynthetic capabilities of a selective microorganisms, which in a specific example is Chlorobium thiosulfatophilum, is shown in FIG. 3. The reactor 100 includes a hollow container having a front wall 112, a rear wall 114 and a cylindrical side wall 116. A first reactor sector 118 comprising lower portions 112a, 114a and 116a, respectively, of the front, rear and side walls is adapted to contain a liquid nutrient material 121 for the microorganism.

A second sector 122 of the reactor is comprised of the upper portions 112b, 114b and 116b, respectively, of the front, rear and side walls. The upper cylindrical side wall 116b is at least translucent and preferably transparent to the radiation emitted by a pair of infrared light sources 124 and 126 mounted above the upper side wall 116b.

A plurality of cylindrical discs 134 are rotatably mounted on a shaft 136 which is journaled in the front and rear walls 112 and 114 of the reactor. The discs 134 carry a high area fiber webbing 132 as previously described. Each support disc has at least one hollow tube 138 extending between the centrally located shaft 136 and the outer periphery of the support disc 134. Each tube 138 is provided with a plurality of holes 140 which function to intake liquid nutrient and the gas stream to be treated when the tube is located in the reactor sector 118 and subsequently, when the tube is located in the reactor sector 122, to distribute the nutrient and gas over the webbing 132 in the manner previously described in connection with the embodiments shown in FIGS. 1 and 2.

In operation of the reactor 100 is first necessary to prepare a culture by sterilizing, inoculating, and incubating a liquid solution 121 of microorganism nutrients. The selected microorganism such as Chlorobium thiosulfatophilum is then transferred to the solution by any suitable manner well known to those skilled in the art and incubated at a suitable temperature. The culture is then pumped (by means not shown) through input port 128 into the first reactor section 118 where it starts a rapid growth attached to the fiber webbing 132. The discs 134 are rotated through the culture by a motor 142 at a rate sufficient for thorough mixing without causing the microorganism to become detached from the webbing 132 for a time period sufficient to produce a satisfactory chemical yield.

When the microorganism growth completely covers the fiber webbing 32, the light sources 124 and 126, which provide infrared light are turned on and a gas stream comprising a blend of H$_2$S, CO$_2$ and N$_2$ is introduced under pressure into the reactor sector 118 through the input port 128. The gas particles are mixed with the liquid nutrient solution and flow into the tube 138 through the holes 140 when the tube is located in the reactor sector 118. When the tube 138 is located in reactor section 122 the nutrient solution and gas particles are distributed over the fiber webbing 132 where infrared light from the sources 124 and 126 initiates a photosynthetic anaerobic bioprocess defined by the equation $$2H_2S + CO_2 \rightarrow 2S^\circ + (CH_2O) + H_2O$$

The othorombic sulfur excreted by Chlorobium together with excess biomass which accumulates on the fiber webbing 132 is washed by nozzles 143 to the bottom of the reactor sector 118 where it is removed by a screw conveyor 144 through an output port 146 to a sedimentation tank 148. In the sedimentation tank Cholorobium cells, separated from the sulfur, are either recycled back to the reactor 100 or directed to a bypass 150 to recover a biomass product.

The reactor shown in FIG. 3 can also be used to produce molecular hydrogen using the photometabolically active microbes *Rhodospirillum rubrum* as described in the aforementioned U.S. Pat. No. 4,010,076 to Weetall, *Rhodopseudomonas Miami* PBE 2271 as described in a paper entitled "Seawater—Based Hydrogen Production By Immobilized Marine Photosynthetic Bacteria" presented at the Gattinburg Conference on Biotechnology May 11-14, 1982, Chromatium Miami PBS 1071 as described in an article entitled "Hydrogen Production by Marine Photosynthetic Bacteria: Effect Of Environmental Factors and Substrate Specificity On The Growth Of A Hydrogen Producing Marine Photosynthetic Bacterium" published in the International Journal of Hydrogen Energy, Vol. 6, No. 5, pp. 451-460, 1981, and *Oscillatoria Miami* BG7 as described in an article entitled "Characterization and Optimization Of Hydrogen Photoproduction By A Salt Water Blue-Green Alga, *Oscillatoria Miami* BG7, I Enhancement Through Limiting The Supply Of Nitrogen Nutrients" published in the International Journal of Hydrogen Energy, Vol. 6, No. 4, pp. 339-348, 1981.

Using *R. rubrum* as the microbe and malate as the nutrient medium the reaction is as follows:

$$C_4H_6O_5 + 3H_2O \rightarrow 4CO_2 + 6H_2$$

The cells of *R. rubrum* are grown as described in the Weetall Patent and attached to the fiber webbing 132. Then an aqueous malate solution is pumped into the container sector 118 under anaerobic conditions. The malate solution is drawn into the tube 138 when the tube is located in the reactor section 118 and evenly distributed over the webbing 132 when the tube 138 is located in the container section 122 where visible light from the light sources 124 and 126 initiates a photometabolic reaction to yield hydrogen which is withdrawn through output port 152.

The invention has been described in detail with particular reference to illustrative preferred embodiments thereof, but it will be understood that variations and modifications can be effected within the spirit and scope of the invention.

I claim:

1. Apparatus for photochemically reacting a selected fluid comprising:
    (a) a hollow container, said container comprising a first lower section containing a volume of the selected fluid and a second upper section having at least one light transmitting wall;
    (b) a shaft supported for rotation in said container;
    (c) a plurality of porous support disks mounted on said shaft so that a first portion of each support disk extends into said lower container section and a second portion of each support disk extends into said upper container section;
    (d) webbing means attached to each of said support disks, said webbing means comprising a multiplicity of high surface area fibers suitable for attaching said fluid and having a diameter of about ⅛ inch or less;
    (e) a light source located adjacent said light transmitting wall, said light source emitting radiation of a selected wave length for exciting selected molecules of said fluid; and
    (f) means for rotating said shaft so that portions of said webbing means are sequentially immersed in the volume of fluid contained in said lower container section and then moved out of said fluid volume and into said upper container section whereat said fluid is exposed to radiation from said light source.

2. The apparatus according to claim 1 wherein the multiplicity of fibers are in the form of fiberglass.

3. The apparatus according to claim 1 wherein the multiplicity of fibers are in the form of ceramic material.

4. The apparatus according to claim 1 wherein the multiplicity of fibers are in the form of a polyester.

5. The apparatus according to claim 1 wherein said light source comprises a source of ultraviolet light.

6. Apparatus for photochemically reacting a selected nutrient fluid with a selected photometabolic microorganism suitable for converting a selected component of the nutrient fluid into a selected chemical, said apparatus comprising:
    (a) a hollow container, said container comprising a first lower section containing a volume of the selected nutrient fluid and a second upper section having at least one light transmitting wall;
    (b) a shaft supported for rotation in said container;
    (c) a plurality of porous support disks mounted on said shaft so that a first portion of each support disk extends into said lower container section and a second portion of each support disk extends into said upper container section;
    (d) webbing means attached to each of said support disks, said webbing means comprising a multiplicity of high surface area fibers suitable for attaching said microorganism and having a diameter of about ⅛ inch or less;
    (e) a light source located adjacent said light transmitting wall, said light source emitting radiation of a selected wave length for photometabolically exciting said microorganism;
    (f) means for rotating said shaft so that portions of said webbing means are sequentially immersed in the volume of nutrient fluid contained in said lower container section and then moved out of said nutrient fluid volume and into said upper container section whereat said microorganism is exposed to the radiation from said light source, said shaft being rotated at a speed which is below the speed at which the microorganism becomes detached from said webbing while providing exposure of the microorganism and the selected nutrient fluid component for a time period sufficient to produce a satisfactory chemical yield;
    (g) a discharge port for the selected chemical, and
    (h) means for removing the selected chemical from said container through said discharge port.

7. The apparatus according to claim 6 wherein said light source comprises a source of infrared light.

8. The apparatus according to claim 6 wherein said support disks include a hollow tube having a plurality of holes therein for intaking the selected fluid and the selected microorganism when said hollow tube is rotated through said first lower container section and for evenly distributing the selected fluid and the selected microorganism over said high area fibers when said hollow tube is rotated through said second upper container section.

* * * * *